United States Patent [19]
Saitoh et al.

[11] Patent Number: 6,040,335
[45] Date of Patent: Mar. 21, 2000

[54] THERAPEUTICS FOR THROMBOCYTOPENIA

[75] Inventors: Masayuki Saitoh; Yasuo Kitajima, both of Osaka; Norio Iwasawa, Shiga-ken; Kenju Miura; Munetada Haruyama, both of Osaka; Junko Hashino, Kyoto, all of Japan

[73] Assignee: Suntory Limited, Osaka, Japan

[21] Appl. No.: 08/849,887

[22] PCT Filed: Oct. 17, 1996

[86] PCT No.: PCT/JP96/03008

§ 371 Date: Jul. 31, 1997

§ 102(e) Date: Jul. 31, 1997

[87] PCT Pub. No.: WO97/14704

PCT Pub. Date: Apr. 24, 1997

[30] Foreign Application Priority Data

Oct. 17, 1995 [JP] Japan .................................. 7-268644

[51] Int. Cl.$^7$ ..................... A61K 31/365; C07D 309/02
[52] U.S. Cl. ........................................... 514/460; 549/222
[58] Field of Search .............................. 549/222; 514/460

[56] References Cited

U.S. PATENT DOCUMENTS

| | | | |
|---|---|---|---|
| 4,235,913 | 11/1980 | Johnson et al. | 546/269 |
| 4,725,602 | 2/1988 | Carson | 514/351 |
| 5,334,587 | 8/1994 | Kohama et al. | 514/99 |
| 5,409,912 | 4/1995 | Sugimura et al. | 549/222 |

FOREIGN PATENT DOCUMENTS

| | | |
|---|---|---|
| 1-304893 | 12/1989 | Japan . |
| 2-186 | 1/1990 | Japan . |
| 5-213758 | 8/1993 | Japan . |
| 7-2886 | 1/1995 | Japan . |
| 8-41087 | 2/1996 | Japan . |

OTHER PUBLICATIONS

CA 110:29472, Furuhama et al., 1994.
Ishibashi et al., "Interleukin–6 is A Potent Thrombopoietic Factor In Vivo In Mice", Blood, vol. 74, No. 4, 1989, pp 1241–1244.
Asano et al., "In Vivo Effects of Recombinant Human Interleukin–6 in Primates: Stimulated Production of Platelets", Blood, vol. 75, No. 8, 1990, pp 1602–1605.
Okada et al., "In Vivo Anti–Tumor Effect By The Transfection With IL–6 Gene", Ketsueki Shuyoka, 1991, pp. 22:23–31.
Sauvage et al., "Stimulation of Megakaryocytopoiesis and Thrombopoiesis y The c–Mpl Ligand", Nature, vol. 369, 1994, pp 533–538.
Nakjima et al., "Stimulatory Effect of Romurtide On Hematopoiesis in Monkeys", Arzneim–Forsch/Drug Res., vol. 41, 1991, pp 60–65.
Okawa et al., "Restorative Effect of MDP–Lys (L18) on Leukopenia of Cancer Patient Treated With Radiotherapy", Nihon Igaku Hoshasen Gakkaishi, 1988 48(4) pp 514–523.
Ozasa et al., "Novel Antitumor Antibiotic Phospholine", The Journal of Antibiotics, vol. 42, No. 9, 1989, pp 1331–1343.
Takano et al., "Seimitsu Yukigosei", Nankodo, 1983.
Fushimi et al., "Studies On New Phosphate Ester Antifungal Antibiotics Phoslactomycins", The Journal of Antibiotics, vol. 42, No. 7, 1989, pp 1019–1036.
Abstracts of the 17$^{th}$ Annual Meeting of the Pesticide Science Society of Japan, 1992, p. 39.
Shibata et al., "Preparation of Leustroducsin H and the Structure–Activity Relationship of Its Derivatives", The Journal of Antibiotics, vol. 48, No. 12, 1995, pp 1518–1520.
Shibata et al., "Absolute Configuration of Leustroducsins", Tetrahedron, vol. 51, No. 44, 1995, pp 11999–12012.

*Primary Examiner*—Jane Fan
*Attorney, Agent, or Firm*—Pillsbury Madison & Sutro LLP

[57] ABSTRACT

Compounds represented by the general formula (I) or pharmacologically acceptable salts thereof:

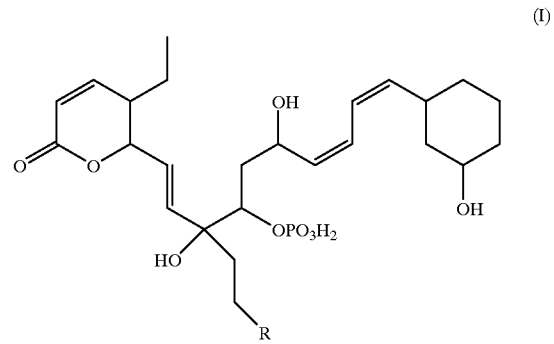

(I)

(where R is a group —NHCHR$_1$R$_2$, —N(CHR$_1$R$_2$)$_2$, —N(CHR$_1$R$_2$)CHR$_3$R$_4$, —N$^+$(CHR$_1$R$_2$)$_3$, —N$^+$(CHR$_1$R$_2$)$_2$CHR$_3$R$_4$ or —N$^+$(CHR$_1$R$_2$)(CHR$_3$R$_4$)CHR$_5$R$_6$ (where R$_1$, R$_2$, R$_3$, R$_4$, R$_5$ and R$_6$, which may be the same or different, are each a hydrogen atom, an alkyl group, an alkenyl group, an aryl group or an aralkyl group, or an alkyl, alkenyl, aryl or aralkyl group which is substituted by at least one substituent selected from the group consisting of a halogen atom, a hydroxyl group, a lower alkoxy group, a lower alkylacyloxy group, a lower alkylacyl group, a lower alkoxycarbonyl group, a nitro group, a cyano group and a heterocyclic group, with CHR$_1$R$_2$, CHR$_3$R$_4$ or CHR$_5$R$_6$ optionally forming a cyclic alkyl group, provided that when R is —N(CHR$_1$R$_2$)CHR$_3$R$_4$, —N$^+$(CHR$_1$R$_2$)$_2$CHR$_3$R$_4$ or —N$^+$(CHR$_1$R$_2$)(CHR$_3$R$_4$)CHR$_5$R$_6$, CHR$_1$R$_2$, CHR$_3$R$_4$ and CHR$_5$R$_6$ are different groups); therapeutics for thrombocytopenia containing them as an effective ingredient; as well as intermediates for their synthesis and processes for producing them.

13 Claims, No Drawings

THERAPEUTICS FOR THROMBOCYTOPENIA

This application is the national phase of international application PCT/JP96/03008, filed Oct. 17, 1996 which designated the U.S. now WO 97/14704 Apr. 24, 1997.

TECHNICAL FIELD

This invention relates to novel 2-pyranone derivatives and pharmacologically acceptable salts thereof, as well as therapeutics for thrombocytopenia containing them as an effective ingredient. The invention also relates to intermediates for their synthesis and processes for producing them.

BACKGROUND ART

Thrombocytopenia is a disease that accompanies immunological disorders or bone marrow damaging metastatic tumors, tuberculosis, leukemia, etc. Alternatively, it is caused by other factors such as the use of chemotherapeutics or radiation therapy. Thrombocytopenia is a serious disease which, when aggravated, causes bleeding in various parts of the body, occasionally leading to death.

Symptomatic therapy by platelet transfusion is currently considered to be the sole reliable method that can treat thrombocytopenia and it is desired to develop therapeutics that can increase platelets per se.

In recent years, reports have been made that show the platelet increasing action of cytokines such as interleukin-6, interleukin-11 and leukemia inhibitory factor (LIF) (Ishibashi et al., Blood, 74:1241–1244, 1989; Asano et al., Blood, 75:1602–1605, 1990; Zenji Okada et al., KETUEKI SHUYOKA, 22:23–31, 1991). However, the production of these cytokines is regulated and controlled by various cells within the body and if they are externally administered to the body, the balance in regulation is upset, eventually causing serious side effects such as damage to the liver.

It has also been suggested recently that a protein called "thrombopoietin (TPO)" is a factor that increases megakaryocytes and platelets (see, for example, Sauvage et al., Nature, 369:533–538, 1994), however, clinical effects of this protein have not yet been verified.

Derivatives such as muramyl dipeptide are known as low-molecular weight compounds that increase the platelet count (Nakajima et al., Arzneim.-Forsch./Drug Res. 41:60–65, 1989). It is postulated that these derivatives increase platelets by activating monocytes and macrophages so as to produce interleukin-6. However, it has also been reported that the administration of derivatives such as muramyl dipeptide also triggers other physiological activities based on the activation of macrophages, thereby causing fever and other side effects (NIHON IGAKU HOSHASEN GAKKAISHI, 48(4):514, 1988).

The compounds structurally similar to the compounds of the invention are taught in Japanese Patent Public Disclosure Nos. 304893/1989 and 186/1990, as well as The Journal of Antibiotics, 42:1331–1343, 1989; they are 2-pyranone derivatives obtained as the metabolites of actinomyces of the genus Streptomyces and these compounds have been reported to have an antimicrobial action against plant pathogenic fungi, as well as cytotoxicity to leukemic cells.

In addition, Japanese Patent Public Disclosure Nos. 213758/1993 and 2886/1995 teach that 2-pyranone derivatives are compounds exhibiting a platelet increasing action in mouse. However, these compounds are not necessarily satisfactory in terms of safety.

An object of the invention is to overcome the aforementioned defects of the prior art by providing compounds that are safe and which have an action for increasing platelets per se.

DISCLOSURE OF INVENTION

The present inventors conducted intensive studies on various compounds with a view to solving the aforementioned problems and found novel 2-pyranone derivatives that had a platelet increasing action in mouse and which yet had low toxicity. The present invention has been accomplished on the basis of this finding.

Thus, the present invention provides compounds represented by the general formula (I) or pharmacologically acceptable salts thereof:

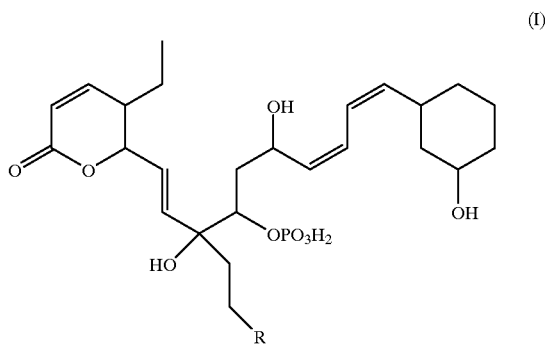

(I)

(where R is a group —NHCHR$_1$R$_2$, —N(CHR$_1$R$_2$)$_2$, —N(CHR$_1$R$_2$)CHR$_3$R$_4$, —N$^+$(CHR$_1$R$_2$)$_3$, —N$^+$(CHR$_1$R$_2$)$_2$CHR$_3$R$_4$ or —N$^+$(CHR$_1$R$_2$)(CHR$_3$R$_4$)CHR$_5$R$_6$ (where R$_1$, R$_2$, R$_3$, R$_4$, R$_5$ and R$_6$, which may be the same or different, are each a hydrogen atom, an alkyl group, an alkenyl group, an aryl group or an aralkyl group, or an alkyl, alkenyl, aryl or aralkyl group which is substituted by at least one substituent selected from the group consisting of a halogen atom, a hydroxyl group, a lower alkoxy group, a lower alkylacyloxy group, a lower alkylacyl group, a lower alkoxycarbonyl group, a nitro group, a cyano group and a heterocyclic group, with CHR$_1$R$_2$, CHR$_3$R$_4$ or CHR$_5$R$_6$ optionally forming a cyclic alkyl group, provided that when R is —N(CHR$_1$R$_2$)CHR$_3$R$_4$, —N$^+$(CHR$_1$R$_2$)$_2$CHR$_3$R$_4$ or —N$^+$(CHR$_1$R$_2$)(CHR$_3$R$_4$)CHR$_5$R$_6$, CHR$_1$R$_2$, CHR$_3$R$_4$, and CHR$_5$R$_6$ are different groups)).

The invention also provides therapeutics for thrombocytopenia that contain those compounds or pharmcologically acceptable salts thereof, as well as intermediates for their synthesis and processes for producing them.

With the 2-pyranone derivatives (I) of the invention, preferred examples of R$_1$, R$_2$, R$_3$, R$_4$, R$_5$ and R$_6$ include the following: exemplary alkyl groups are straight-chained or branched lower alkyl groups such as methyl, ethyl, n-propyl, isopropyl, n-butyl, tert-butyl, hexyl and octyl groups; exemplary alkenyl groups are straight-chained or branched lower alkenyl groups such as vinyl, allyl, 1-propenyl, 2-butenyl and 2-methyl-2-propenyl groups; exemplary aryl groups are C$_{6-10}$ aryl groups such as phenyl, tolyl, xylyl, mesityl, cumenyl and naphtyl groups; and exemplary aralkyl groups are C$_{7-24}$ aralkyl groups such as benzyl, phenethyl, trityl and benzhydryl groups. Examples of the cyclic alkyl group formed by CHR$_1$R$_2$, CHR$_3$R$_4$ or CHR$_5$R$_6$ include mono- or polycyclic alkyl groups such as cyclopentyl, cyclohexyl, cycloheptyl, menthyl, phentyl and bornyl groups. Unless otherwise noted, the term "lower" as used herein means preferably 1–8 carbon atoms, with the range of 1–4 carbon atoms being particularly preferred.

The above-defined alkyl, alkenyl, aryl and aralkyl groups may be substituted with the following: halogen atoms such as fluorine, chlorine and bromine atoms; a hydroxyl group; lower alkoxy groups such as methoxy, ethoxy and propoxy groups; lower alkylacyloxy groups such as acetoxy and propionyloxy groups; lower alkylacyl groups such as acetyl, propionyl and butyryl groups; lower alkoxycarbonyl groups such as methoxycarbonyl, ethoxycarbonyl and propoxycarbonyl groups; a nitro group, a cyano group; and heterocyclic groups which are preferably unsaturated mono-heterocyclic groups such as pyrrolyl, pyridyl, pyrazolyl, imidazolyl, pyridazinyl, pyrimidinyl, pyrazinyl, triazolyl (e.g., 4H-1,2,4-triazolyl), tetrazolyl (e.g., 1H-tetrazolyl or 2H-tetrazolyl), furyl, thiophenyl, benzofuranyl, benzothiophenyl, oxazolyl, isoxazolyl, thiazolyl, indolyl, benzothiazolyl, benzimidazolyl and quinolyl. These heterocyclic groups may be bound by carbon atoms or, alternatively, they may be bound by nitrogen atoms to form intramolecular quaternary salts.

The 2-pyranone derivatives (I) of the invention may be used in the form of pharmacologically acceptable nontoxic salts with inorganic metals such as alkali metals (e.g. sodium and potassium) and alkaline earth metals (e.g. calcium and magnesium); basic amino acids such as lysine and arginine; and organic amines such as ammonium.

Further, the 2-pyranone derivatives (I) of the invention can be used in the form pharmacologically acceptable non-toxic acid addition salts. Such acid addition salts include, but are not limited to, inorganic acid salts such as hydrochlorides, sulfates, hydrobromides and phosphates; organic acid salts such as formates, acetates, succinates, maleates, fumarates, malates, mandelates, glutamates, aspartates, methanesulfonates and p-toluenesulfonates.

The 2-pyranone derivatives (I) of the invention and the compounds represented by the general formula (II) to be set forth below which are used as intermediates for synthesis of those derivatives have various isomers and in the present invention, all of these possible isomers and mixtures thereof are embraced.

BEST MODE FOR CARRYING OUT THE INVENTION

The 2-pyranone derivatives (I) of the invention can be produced by combining the N-alkylation reaction and the hydrolytic reaction of esters. Examples of the N-alkylation reaction include (1) the amine mediated nucleophilic substitution with alkyl halides, alkylsulfonate ester or alkyl sulfates and (2) the reductive alkylation between aldehydes or ketones and amines in the presence of reducing agents, as described in "SEIMITSU YUKIGOSEI" (Seiichi Takano & Kunio Ogasawara, Nankodo, 1983). Examples of the hydrolytic reaction of esters include 1) hydrolysis using hydrolases such as esterase and lipase and 2) hydrolysis using bases such as sodium hydroxide, sodium hydrogen carbonate and sodium carbonate, as described in Japanese Patent Public Disclosure No. 2886/1995. More preferably, the reductive alkylation in the presence of a ketone or aldehyde and a reducing agent or the amino group mediated nucleophilic substitution with an alkyl halide may be combined with the hydrolytic reaction with a hydrolase or base to design a production process comprising the following steps A–I:

Step A: Compounds represented by the general formula (III):

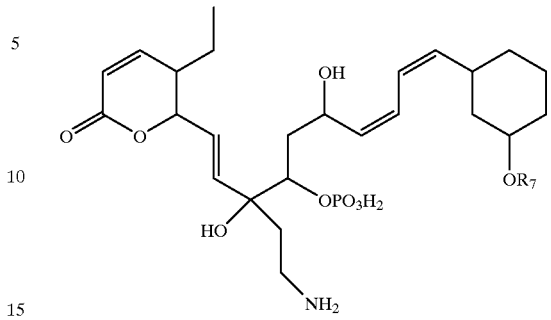

(where $R_7$ is an acyl group), either singly or in admixture, are subjected to reductive alkylation reaction with a ketone or aldehyde of the general formula:

$R_1COR_2$ and/or $R_3COR_4$ (where $R_1$, $R_2$, $R_3$ and $R_4$, which may be the same or different, are each a hydrogen atom, an alkyl group, an alkenyl group, an aryl group or an aralkyl group, or an alkyl, alkenyl, aryl or aralkyl group which is substituted by at least one substituent selected from the group consisting of a halogen atom, a hydroxyl group, a lower alkoxy group, a lower alkylacyloxy group, a lower alkylacyl group, a lower alkoxycarbonyl group, a nitro group, a cyano group and a heterocyclic group, with $R_1$ and $R_2$ or $R_3$ and $R_4$ being optionally taken together to form an alkylene group, provided that $R_1COR_2$ is different from $R_3COR_4$) in the presence of a reducing agent to prepare a compound represented by the general formula (IIa):

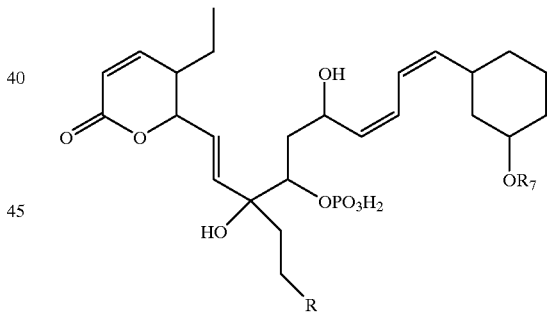

(where R is a group —NHCHR$_1$R$_2$, —N(CHR$_1$R$_2$)$_2$ or —N(CHR$_1$R$_2$)CHR$_3$R$_4$ (where $R_1$, $R_2$, $R_3$ and $R_4$ are the same as defined above, provided that when R is —N(CHR$_1$R$_2$)CHR$_3$R$_4$, CHR$_1$R$_2$ and CHR$_3$R$_4$ are different groups); and $R_7$ is the same as defined above).

In compound (III), the acyl group has a carbonyl group bound to a carbon atom in an organic group. In preferred examples of the acyl group, the organic group is a straight-chained, branched or mono- or polycyclic aliphatic group that have 1–15 carbon atoms, and more preferred examples include butyryl, isobutyryl, isovaleryl, 2-methylbutyryl, 4-methylvaleryl, cyclohexanecarbonyl, 4-methylhexanoyl, 5-methylhexanoyl, 6-methylheptanoyl, cyclohexylethylcarbonyl, octanoyl, 6-methyloctanoyl and 7-methyloctanoyl groups.

Step B: Compound (IIa) is subjected to an ester hydrolysis reaction using 1) a hydrolase such as porcine liver esterase or lipase or 2) a base such as sodium hydroxide, sodium hydrogencarbonate or sodium carbonate to prepare the end compound represented by the general formula (Ia):

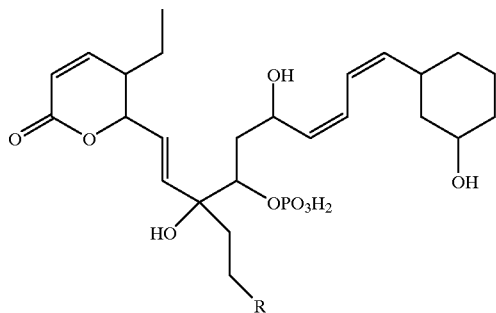

(Ia)

(where R is a group —NHCHR$_1$R$_2$, —N(CHR$_1$R$_2$)$_2$ or —N(CHR$_1$R$_2$)CHR$_3$R$_4$ (where R$_1$, R$_2$, R$_3$ and R$_4$ are the same as defined above)).

Step C: Compound (III) is hydrolyzed by the same procedure as in step B to prepare a compound represented by the formula (IV):

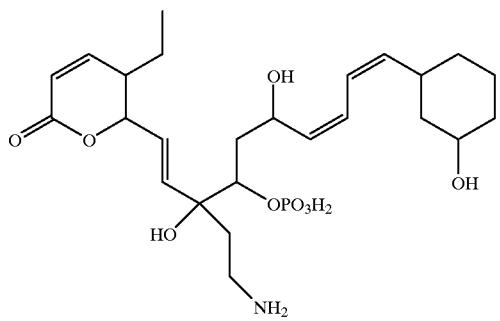

(IV)

Step D: Compound (IV) is alkylated reductively by the same procedure as in step A to prepare the end compound (Ia).

Step E: Compound represented by the general formula (Ia):

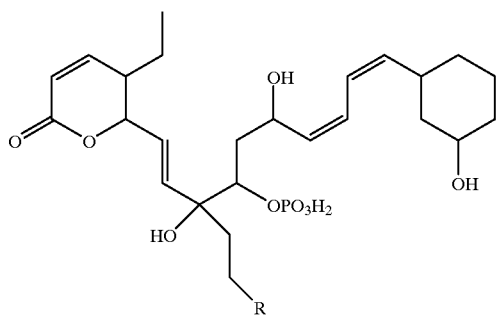

(Ia)

(where R is a group —NHCHR$_1$R$_2$, —N(CHR$_1$R$_2$)$_2$ or —N(CHR$_1$R$_2$)CHR$_3$R$_4$ (where R$_1$, R$_2$, R$_3$ and R$_4$ are the same as defined above) is subjected to the amino group mediated nucleophilic substitution with a compound represented by the general formula R$_1$R$_2$CHX, R$_3$R$_4$CHX and/or R$_5$R$_6$CHX (where R$_1$, R$_2$, R$_3$, R$_4$, R$_5$ and R$_6$, which may be the same or different, are such that R$_1$, R$_2$, R$_3$ and R$_4$ are the same as defined above and that R$_5$ and R$_6$ are each a hydrogen atom, an alkyl group, an alkenyl group, an aryl group or an aralkyl group, or alkyl, alkenyl, aryl or aralkyl group which is substituted by at least one substituent selected from the group consisting of a halogen atom, a hydroxyl group, a lower alkoxy group, a lower alkylacyloxy group, a lower alkylacyl group, a lower alkoxycarbonyl group, a nitro group, a cyano group and a heterocyclic group, which CHR$_5$R$_6$ optionally forming a cyclic alkyl group, provided that R$_1$R$_2$CHX, R$_3$R$_4$CHX and R$_5$R$_6$CHX are different from one another; and X is a halogen atom) to prepare the end compound represented by the general formula (Ib):

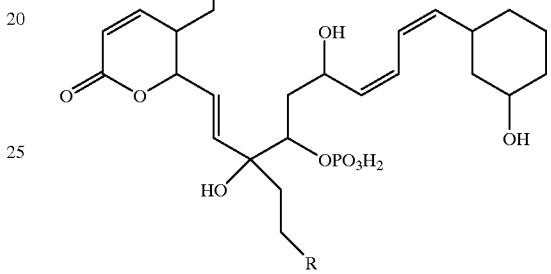

(Ib)

(where R is a group —N$^+$(CHR$_1$R$_2$)$_3$, —N$^+$(CHR$_1$R$_2$)$_2$CHR$_3$R$_4$ or —N$^+$(CHR$_1$R$_2$)(CHR$_3$R$_4$)CHR$_5$R$_6$ (where R$_1$, R$_2$, R$_3$, R$_4$, R$_5$ and R$_6$ are the same as defined above)).

Step F: Compound (IV) is subjected to the amino group mediated nucleophilic substitution with a compound represented by the general formula R$_1$R$_2$CHX (where R$_1$ and R$_2$, which may be the same or different, are each a hydrogen atom, an alkyl group, an alkenyl group, an aryl group or an aralkyl group, or an alkyl, alkenyl, aryl or aralkyl group which is substituted by at least one substituent selected from the group consisting of a halogen atom, a hydroxyl group, a lower alkoxy group, a lower alkylacyloxy group, a lower alkylacyl group, a lower alkoxycarbonyl group, a nitro group, a cyano group and a heterocyclic group, with CHR$_1$R$_2$ optionally forming a cyclic alkyl group) to prepare the end compound represented by the general formula (Ic):

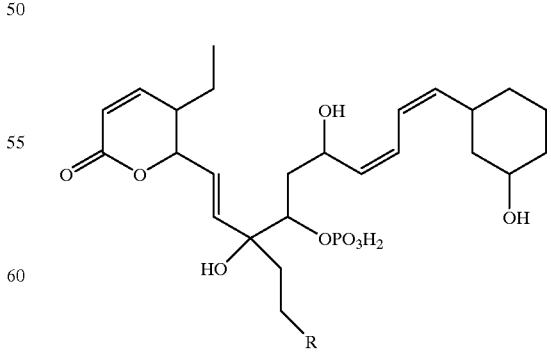

(Ic)

(where R is a group —NHCHR$_1$R$_2$, —N(CHR$_1$R$_2$)$_2$ or —N$^+$(CHR$_1$R$_2$)$_3$ (where R$_1$ and R$_2$ are the same as defined above)).

Step G: Compound (IIa) is treated by the same procedure as in step E to prepare a compound represented by the general formula (IIb):

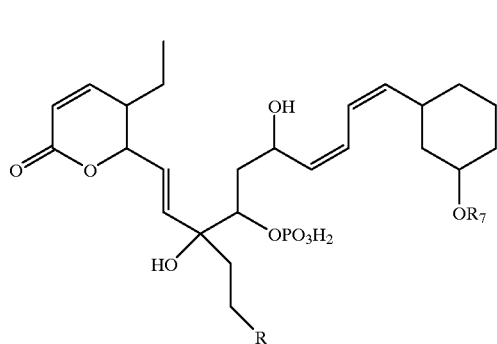

(IIb)

(where R is a group —N$^+$(CHR$_1$R$_2$)$_3$, —N$^+$(CHR$_1$R$_2$)$_2$CHR$_3$R$_4$ or —N$^+$(CHR$_1$R$_2$)(CHR$_3$R$_4$)CHR$_5$R$_6$ (where R$_1$, R$_2$, R$_3$, R$_4$, R$_5$ and R$_6$ are the same as defined above); and R$_7$ is the same as defined above).

Step H: Compound (III) is treated by the same procedure as in step F to prepare a compound represented by the general formula (IIc):

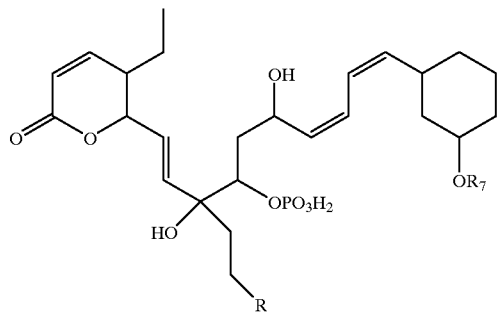

(IIc)

(where R is a group —NHCHR$_1$R$_2$, —N(CHR$_1$R$_2$)$_2$ or —N$^+$(CHR$_1$R$_2$)$_3$ (where R$_1$ and R$_2$ are the same as defined above); and R$_7$ is the same as defined above).

Step I: Compound (IIb) is hydrolyzed by the same procedure as in step B to prepare the end compound (Ib). The same procedure may be employed to prepare the end compound (Ic) from compound (IIc).

It should be mentioned that steps E and G may be carried out without isolating compounds (Ia) and (IIa) which are respectively obtained in step D (or B) and step A but subjecting them as such to the associated reactions.

The above-described production processes of the invention are summarized in the following charts.

CHART 1

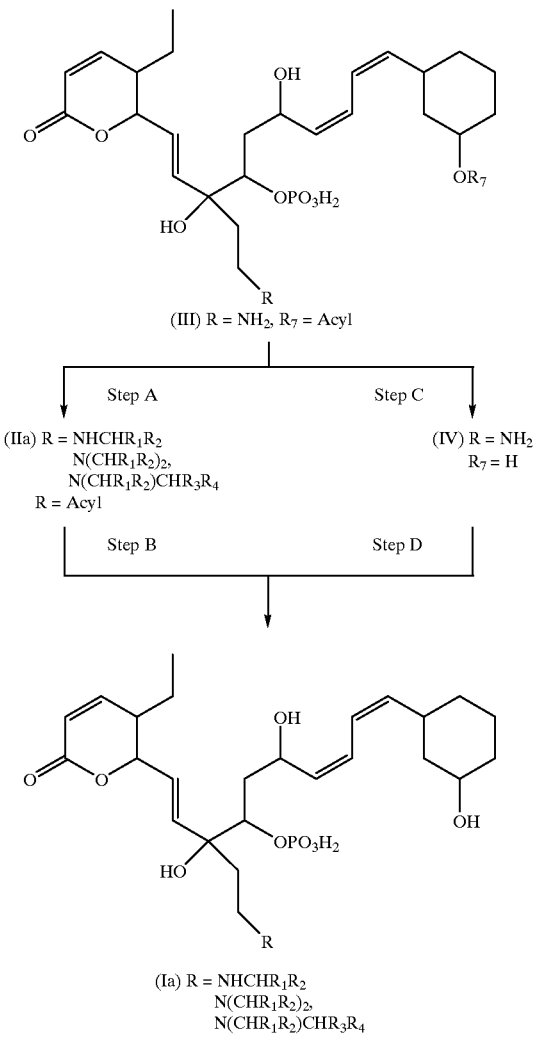

CHART 2

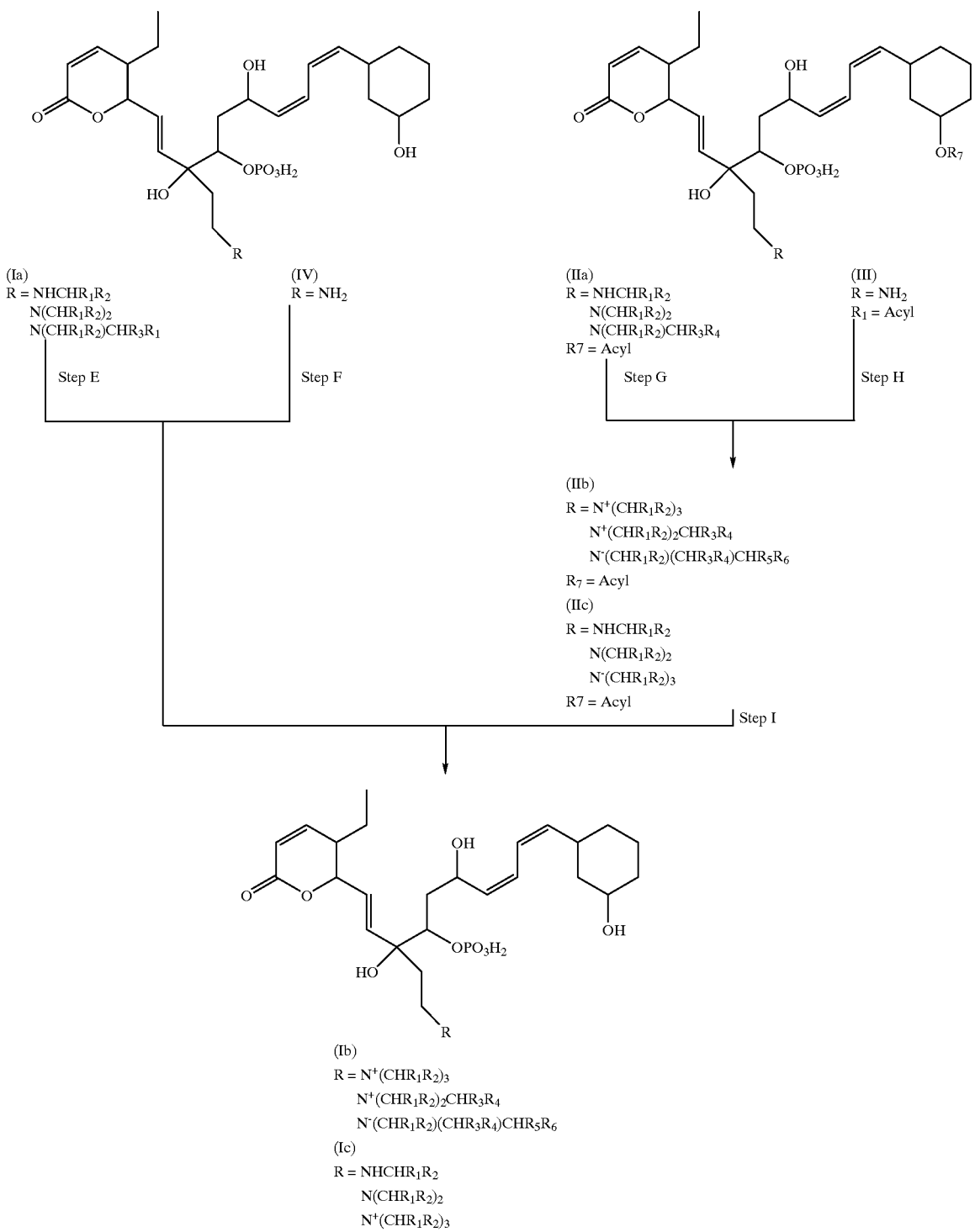

It should be noted that the 2-pyranone derivatives of the general formula (III) which are used as the starting compound for the production process described above are all known and may be found in J. Antibiotics, 42:1019–1036, 1989, as well as Japanese Patent Public Disclosure Nos. 304893/1989 and 213758/1993. The 2-pyranone derivative of the formula (IV) is also a known compound which was initially reported to have an antimicrobial activity (Abstracts of the 17th Annual Meeting of the Pesticide Science Society of Japan, p. 39, 1992) and which was recently reviewed for its platelet increasing action (Japanese Patent Public Disclosure No. 2886/1995).

In order to perform the N-alkylation reaction in the above-described process reductively, the starting compound (III) or (IV) may be reacted with a ketone or aldehyde of the general formula $R_1COR_2$ or $R_3COR_4$, preferably in an amount of 1–5 moles per mole of the starting compound, in the presence of a reducing agent preferably sodium cyanoborohydride, lithium cyanoborohydride or formic acid, preferably in an amount of 0.6–2 moles. Any solvents that dissolve the starting compound without interfering with the reaction may be used without particular limitations and preferred examples include alcohols such as methanol and ethanol, dimethylformamide and water, which may be used in admixture. Depending on the case, absolute alcohols or alcoholic solutions of acids such as hydrochloric acid may be added in order to enhance the efficiency of the reaction. The reaction temperature varies with the solvent, reducing agent and the starting material used, etc. and the range of 0–40° C. is preferred. The reaction time also varies with the solvent, reducing agent and starting material used, etc. and it typically ranges from 30 min to 72 hr. After the end of the reaction, the product may be recovered by removing the solvent, adsorbing the residual solution on a column such as SepPack C18 (Waters), eluting with a solvent such as methanol, optionally fractionating by column chromatography as required and then freeze-drying the eluate. For reacting the starting compound (III) or (IV) with the ketone or aldehyde of the general formula $R_1COR_2$ or $R_3COR_4$, a two-stage reaction may be adopted in consideration of the reaction affinity.

The amino group mediated nucleophilic substitution can be implemented by reacting a reactant alkyl halide with the starting compound (Ia), (IIa), (III) or (IV) in an inert solvent in the presence or absence of a base. Examples of the base that can be used include metal bases such as potassium carbonate, sodium carbonate, sodium hydrogen carbonate, potassium hydroxide and sodium hydroxide, and organic bases such as triethylamine, trimethylamine, diisopropylethylamine and pyridine. Examples of the inert solvent that can be used include methanol, ethanol, propanol, tetrahydrofuran and dimethylformamide. The reaction temperature is preferably 10–100° C. The reaction time which varies with the solvent, base and the starting materials used, etc. usually ranges from 30 min to 3 days. After the end of the reaction, the product may be recovered by removing the solvent from the reaction solution under vacuum in the usual manner and fractionally purifying the residue by column chromatography.

In order to perform the ester hydrolytic reaction in the above-described process by means of a hydrolase, the starting compound (II) or (III) may be reacted with a hydrolase, preferably selected from (but by no means limited to) porcine liver esterase, lipase, acetyl esterase, Takadiastase or cholesterol esterase in a solvent. Preferred examples of the solvent that can be used are mixtures of organic solvents such as alcohols (e.g., methanol and ethanol) or ketones (e.g., acetone and methyl ethyl ketone) with buffer solutions at pH of 6–8. The reaction temperature which varies with the enzyme used is preferably 10–40° C. The reaction time which varies with the solvent, enzyme and the starting material used, etc. usually ranges from 12 hr to 30 days. After the end of the reaction, the product may be recovered by adsorbing the enzyme-removed reaction mixture on a column such as SepPack C18, eluting with a solvent such as methanol, further fractionating by column chromatography as required, and freeze-drying the eluate.

In order to perform the ester hydrolytic reaction by means of a base, the starting compound (II) or (III) may be reacted with a base preferably selected from (but by no means limited to) alkali metal carbonates such as sodium carbonate, potassium carbonate, cesium carbonate and lithium carbonate, alkali metal hydrogencarbonates such as sodium hydrogencarbonate, potassium hydrogencarbonate and lithium hydrogencarbonate, alkali metal hydroxides such as sodium hydroxide, potassium hydroxide and lithium hydroxide, and alkaline earth metal hydroxides such as barium hydroxide and calcium hydroxide in a solvent. Preferred examples of the solvent that can be used are mixtures of organic solvents such as alcohols (e.g., methanol and ethanol) and ketones (e.g., acetone and methyl ethyl ketone) with water. The reaction temperature which varies with the base used is preferably 10–40° C. The reaction time which varies with the solvent, base and the starting material used, etc. usually ranges from 3 hr to 5 days. After the end of the reaction, the product may be recovered by removing the water-miscible organic solvent such as acetone from the reaction solution under vacuum, performing extraction on the aqueous layer with an organic solvent such as ethyl acetate and fractionally purifying the aqueous layer by column chromatography.

The novel 2-pyranone derivatives of the invention can be used as therapeutics for thrombocytopenia. Therapeutics for thrombocytopenia are drugs which, when administered into humans, can induce platelet production in the body to thereby treat the thrombocytopenia caused by various reasons.

The measurement of platelet increasing activity can be implemented by the method described in Ishibashi, T. et al, Blood, 74(4):1241–1244, 1989 or modifications thereof. For example, an animal for platelet measurement such as mouse (e.g. C57BL/6 mouse), rat, dog or monkey is administered intraperitoneally with a test drug as dissolved in ethanolic physiological saline or dimethyl sulfoxide (hereunder sometimes referred to as DMSO) at a suitable concentration. The frequency of administration is usually once or twice a day for 5–10 continuous days; a blood sample is taken from the orbital venous plexus several hours after the final administration and the platelet count is determined. Administration may be performed by any methods including oral, intravenous, intramuscular and subcutaneous routes. The interval of administrations, their frequency and the number of days on which the administration is made are also variable with the drug under test. Platelet count can be determined by an electrical impedance method using a multi-channel automatic platelet counter (e.g., COULTER COUNTER Model JT of Coulter Corporation).

The novel 2-pyranone derivatives of the invention may be administered in various dosage forms, including those for oral administration such as tablets, capsules, granules, powders and syrups, and those for parenteral administration such as injections (i.v., i.m. and s.c.), infusions and suppositories. These various pharmaceutical preparations can be formulated by combining the compounds of the invention with suitable excipients, binders, disintegrators, lubricants, flavoring agents, coloring agents, solubilizing agents, suspensions, coating agents, etc.

The compounds of the invention can be administered in doses that are variable with the symptoms of the disease, the age of the patient, his body weight, the method of administration, etc. and the appropriate dose is determined by doctor; usually, the daily dose ranges from 0.01 mg/kg body weight to 20 mg/kg body weight per adult.

The present invention will now be described in greater detail with reference to the following examples, which are by no means intended to limit the scope of the invention.

EXAMPLES

Example 1

Mouse Platelet Increasing Action

C57BL/6 mice (male, 7-week old) were administered intraperitoneally with the following compounds of the invention in 1% DMSO physiological saline or with 1% DMSO physiological saline alone (control) at 24-hr intervals for 5, 7 or 10 continuous days. Blood samples were collected 72-hr after the final administration in the case of 5-day administration, and 4-hr after the final administration in the case of 7 or 10-day administration, and the platelet count was determined by an electrical impedance method.

6-[3,6-Dihydroxy-3-(2-dimethylaminoethyl)-10-(3-hydroxycyclohexyl)-4-(phosphonoxy)-1,7,9-decatrienyl]-5,6-dihydro-5-ethyl-2H-pyran-2-one (the compound described below in Example 3);

6-[3-(2-Diethylaminoethyl)-3,6-dihydroxy-10-(3-hydroxycyclohexyl)-4-(phosphonoxy)-1,7,9-decatrienyl]-5,6-dihydro-5-ethyl-2H-pyran-2-one (the compound described in Example 7);

6-[3,6-Dihydroxy-10-(3-hydroxycyclohexyl)-3-(2-isopropylaminoethyl)-4-(phosphonoxy)-1,7,9-decatrienyl]-5,6-dihydro- 5-ethyl-2H-pyran-2-one (the compound described in Example 9);

6-[3,6-Dihydroxy-10-(3-hydroxycyclohexyl)-3-(2-pentylaminoethyl)-4-(phosphonoxy)-1,7,9-decatrienyl]-5,6-dihydro-5-ethyl-2H-pyran-2-one (the compound described in Example 12);

6-[3-(2-Cyclopentylaminoethyl)-3,6-dihydroxy-10-(3-hydroxycyclohexyl)-4-(phosphonoxy)-1,7,9-decatrienyl]-5,6-dihydro-5-ethyl-2H-pyran-2-one (the compound described in Example 13);

6-[3-(2-Diethanolaminoethyl)-3,6-dihydroxy-10-(3-hydroxycyclohexyl)-4-(phosphonoxy)-1,7,9-decatrienyl]-5,6-dihydro-5-ethyl-2H-pyran-2-one (the compound described in Example 20);

6-[3,6-Dihydroxy-10-(3-hydroxycyclohexyl)-4-(phosphonoxy)-3-(2-trimethylammoniumethyl)-1,7,9-decatrienyl]-5,6-dihydro-5-ethyl-2H-pyran-2-one (the compound described in Example 23);

6-[3-(2-Diallylaminoethyl)-3,6-dihydroxy-10-(3-hydroxycyclohexyl)-4-(phosphonoxy)-1,7,9-decatrienyl]-5,6-dihydro-5-ethyl-2H-pyran-2-one (the compound described in Example 25).

The results obtained are shown in Table 1.

TABLE 1

| Compound | Dose of administration, (mg/kg) | Period of administration, (days) | No. of test animals (n) | Platelet count, (Mean ± S.E. × $10^3/\mu l$) |
|---|---|---|---|---|
| Control | 0 | 7 | 8 | 1070 ± 152 |
| Compound of EX. 3 | 0.03 | 7 | 6 | 1417 ± 159 |
|  | 0.1 | 7 | 7 | 1486 ± 314 |
|  | 1.0 | 7 | 8 | 1532 ± 137 |
| Control | 0 | 7 | 8 | 985 ± 130 |
| Compound of EX. 3 | 0.1 | 10 | 8 | 1280 ± 260 |
|  | 1.0 | 10 | 8 | 1356 ± 156 |
| Control | 0 | 5 | 8 | 1048 ± 137 |
| Compound of EX. 7 | 0.03 | 5 | 8 | 1373 ± 76 |
|  | 0.1 | 5 | 8 | 1686 ± 226 |
|  | 1.0 | 5 | 8 | 1408 ± 427 |
| Control | 0 | 5 | 8 | 1065 ± 94 |
| Compound of EX. 9 | 0.03 | 5 | 8 | 1433 ± 125 |
|  | 0.1 | 5 | 8 | 1818 ± 291 |
|  | 1.0 | 5 | 8 | 1465 ± 244 |
| Control | 0 | 5 | 8 | 1015 ± 104 |
| Compound of EX. 12 | 0.03 | 5 | 8 | 1263 ± 99 |
|  | 0.1 | 5 | 8 | 1623 ± 192 |
|  | 1.0 | 5 | 8 | 1338 ± 236 |
| Control | 0 | 5 | 8 | 1015 ± 156 |
| Compound of EX. 13 | 0.03 | 5 | 8 | 1490 ± 108 |
|  | 0.1 | 5 | 8 | 1765 ± 291 |
|  | 1.0 | 5 | 8 | 1313 ± 293 |
| Control | 0 | 5 | 8 | 1057 ± 146 |
| Compound of EX. 20 | 0.03 | 5 | 8 | 1154 ± 138 |
|  | 0.1 | 5 | 8 | 1325 ± 104 |
|  | 1.0 | 5 | 8 | 1498 ± 192 |
| Control | 0 | 5 | 8 | 1050 ± 119 |
| Compound | 0.1 | 5 | 8 | 1545 ± 294 |

TABLE 1-continued

| Compound | Dose of administration, (mg/kg) | Period of administration, (days) | No. of test animals (n) | Platelet count, (Mean ± S.E. × $10^3/\mu l$) |
|---|---|---|---|---|
| of EX. 23 | 1.0 | 5 | 8 | 1513 ± 425 |
| Control | 0 | 5 | 8 | 1000 ± 82 |
| Compound of EX. 25 | 0.03 | 5 | 8 | 1074 ± 182 |
|  | 0.1 | 5 | 8 | 1506 ± 209 |
|  | 1.0 | 5 | 8 | 1133 ± 170 |

Example 2

Toxicity Test

C57BL/6 mice were administered intravenously with 5 mg/kg of the invention compound of Example 3 and there were no cases of death.

Example 3

6-[3,6-Dihydroxy-3-(2-dimethylaminoethyl)-10-(3-hydroxycyclohexyl)-4-(phosphonoxy)-1,7,9-decatrienyl]-5,6-dihydro-5-ethyl-2H-pyran-2-one Step A: 6-[10-(3-Cyclohexylcarbonyloxy)cyclohexyl-3,6-dihydroxy-3-(2-dimethylaminoethyl)-4-(phosphonoxy)-1,7,9-decatrienyl]-5,6-dihydro-5-ethyl-2H-pyran-2-one A portion (320 mg, 0.5 mmol) of 6-[3-(2-aminoethyl)-10-(3-cyclohexylcarbonyloxy)cyclohexyl-3,6-dihydroxy-4-(phosphonoxy)-1,7,9-decatrienyl]-5,6-dihydro-5-ethyl-2H-pyran-2-one was dissolved in 20 ml of methanol and 0.4 ml (5.0 mM) of formalin (35% formaldehyde in aq. sol.) was added. To the resulting solution, 63 mg (1.0 mM) of sodium cyanoborohydride was added under cooling with ice and then the mixture was stirred at room temperature for 30 min. The solvent was removed under vacuum and the resulting residue was dissolved in 10 ml of water, adsorbed on SepPack C18, washed with 100 ml of water and eluted with 50 ml of methanol. The methanol-eluted fraction was freeze-dried to give 320 mg of a crude product, which was separated by high-performance liquid chromatography (Develosil Packed Column of Nomura Kagaku Co., Ltd.; φ50 mm×300' mm; eluent—the mixture of water and acetonitrile containing 0.05% trifluoroacetic acid). The peaks of interest were combined, diluted with water to 2 times volume, adsorbed on SepPack C18, washed with 100 ml of water and eluted with 50 ml of methanol. The methanol-eluted fraction was freeze-dried to give 170 mg of the titled compound (yield=50%).

Mass spectrum (SIMS): m/z=668(M+H)$^+$, 690(M+Na)$^+$ $^1$HNMR(CD$_3$OD, δ): 0.95(3H,t,J=7.6 Hz), 1.02–2.03 (23H,m), 2.26(2H,m), 2.52–2.67(2H,m), 2.86(6H,s), 3.12 (1H,m), 3.28(1H,m), 4.31(1H,m), 4.69(1H,m), 4.94(1H,m), 5.10(1H,m), 5.31(1H,m), 5.45(1H,m), 5.95–6.19(3H,m), 6.27(2H,m), 7.07(1H,m)

Step B: 6-[3,6-Dihydroxy-3-(2-dimethylaminoethyl)-10-(3-hydroxycyclohexyl)-4-(phosphonoxy)-1,7,9-decatrienyl]-5,6-dihydro-5-ethyl-2H-pyran-2-one A portion (50 mg, 0.07 mmol) of the compound synthesized in step A was dissolved in 18 ml of 0.05 M KH$_2$PO$_4$-NaOH buffer solution (pH 7.0) and 2 ml of methanol; to the solution, 0.5 ml of a suspension of porcine liver derived esterase (30 mg/3 ml) was added and the mixture was shaken overnight at 37° C. The enzyme-removed reaction mixture was adsorbed on SepPack C18, washed with 10 ml of water and eluted with 10 ml of methanol. The methanol-eluted fraction was freeze-dried to give 39 mg of the titled compound (yield=100%).

Mass spectrum (FAB-MS): m/z=556(M–H)$^-$, $^1$HNMR(CD$_3$OD, δ): 0.96(3H,t,J=7.2 Hz), 1.02–2.02 (14H,m), 2.28(1H,m), 2.56(2H,m), 2.85(6H,s), 3.11(1H,m), 3.28(1H,m), 4.31(1H,m), 4.97(1H,m), 5.10(1H,m), 5.30 (1H,m), 5.43(1H,m), 5.95–6.08(3H,m), 6.25(2H,m), 7.08 (1H,m)

Step C: 6-[3-(2-Aminoethyl)-3,6-dihydroxy-10-(3-hydroxycyclohexyl)-4-(phosphonoxy)-1,7,9-decatrienyl]-5,6-dihydro-5-ethyl-2H-pyran-2-one A portion (56 mg, 0.09 mmol) of 6-[3-(2-aminoethyl)-10-(3-cyclohexylcarbonyloxy)cyclohexyl-3,6-dihydroxy-4-(phosphonoxy)-1,7,9-decatrienyl]-5,6-dihydro-5-ethyl-2H-pyran-2-one was treated by the same procedure as described in step B to prepare 46 mg of the titled compound (yield=97%).

Step D: 6-[3,6-Dihydroxy-3-(2-dimethylaminoethyl)-10-(3-hydroxycyclohexyl)-4-(phosphonoxy)-1,7,9-decatrienyl]-5,6-dihydro-5-ethyl-2H-pyran-2-one A portion (50 mg, 0.09 mol) of the compound obtained in step C was treated by the same procedure as described in step A to prepare 30 mg of the titled compound (yield=66%).

Example 4

6-[3-(2-Benzylaminoethyl)-3,6-dihydroxy-10-(3-hydroxycyclohexyl)-4-(phosphonoxy)-1,7,9-decatrienyl]-5,6-dihydro-5-ethyl-2H-pyran-2-one A portion (90 mg, 0.17 mmol) of the compound obtained in step C of Example 3 and 21 mg (0.2 mmol) of benzaldehyde were treated by the same procedure as described in step A of Example 3 to prepare 20 mg of the titled compound (yield=20%).

Mass spectrum (FAB-MS): m/z=618(M−H)$^-$,
$^1$HNMR(CD$_3$OD, δ): 0.94(3H,t,J=7.2Hz), 1.02–2.00 (13H,m), 2.26(1H,m), 2.55(2H,m), 3.08(1H,m), 3.17(1H,m), 3.54(1H,m), 4.18(2H,m), 4.31(1H,m), 4.95(1H,m), 5.07 (1H,m), 5.31(1H,m), 5.44(1H,m), 5.92–6.03(3H,m), 6.26 (2H,m), 7.09(1H,m), 7.47(5H,m)

Example 5

6-[3,6-Dihydroxy-10-(3-hydroxycyclohexyl)-3-(2-octylaminoethyl)-4-(phosphonoxy)-1,7,9-decatrienyl]-5,6-dihydro-5-ethyl-2H-pyran-2-one A portion (90 mg, 0.17 mmol) of the compound obtained in step C of Example 3 and 26 mg (0.2 mmol) of octyl aldehyde were treated by the same procedure as described in step A of Example 3 to prepare 50 mg of the titled compound (yield=46%).

Mass spectrum (FAB-MS): m/z=640(M−H)$^-$
$^1$HNMR(CD$_3$OD, δ): 0.94(3H,m), 0.98(3H,m), 1.02–2.00 (25H,m), 2.21(1H,m), 2.56(2H,m), 2.96(2H,m), 3.04(1H,m), 3.12(1H,m), 3.54(1H,m), 4.31(1H,m), 4.95(1H,m), 5.10 (1H,m), 5.30(1H,m), 5.43(1H,m), 5.94–6.08(3H,m), 6.26 (2H,m), 7.09(1H,m)

Example 6

Pharmaceutical Formulation

The compound (4 g) obtained in Example 3 and mannitol (50 g) were dissolved in water for injection (100 ml) containing 30% (w/w) of polyethylene glycol 400 and the solution was sterilized by filtration method. The filtered solution was dispensed in 1 ml portions into ampules to prepare injections.

Example 7

6-[3-(2-Diethylaminoethyl)-3,6-dihydroxy-10-(3-hydroxycyclohexyl)-4-(phosphonoxy)-1,7,9-decatrienyl]-5,6-dihydro-5-ethyl-2H-pyran-2-one A portion (160 mg, 0.30 mmol) of the compound obtained in step C of Example 3 and 40 μl (0.73 mmol) of acetaldehyde were treated by the same procedure as described in step A of Example 3 to prepare 35 mg of the titled compound (yield=20%).

Mass spectrum (FAB-MS): m/z=586(M+H)$^+$
$^1$HNMR(CD$_3$OD, δ): 0.97(3H,t,J=7.4 Hz), 1.00–2.00 (19H,m), 2.27(1H,m), 2.55(2H,m), 3.07(1H,m), 3.21(5H,m), 3.54(1H,m), 4.31(1H,m), 4.94(1H,m), 5.11(1H,m), 5.31 (1H,m), 5.44(1H,m), 5.97–6.03(3H,m), 6.24(2H,m), 7.08 (1H,m)

Example 8

6-[3,6-Dihydroxy-3-(2-(dipropylaminoethyl)-10-(3-hydroxycyclohexyl)-4-(phosphonoxy)-1,7,9-decatrienyl]-5,6-dihydro-5-ethyl-2H-pyran-2-one A portion (160 mg, 0.30 mmol) of the compound obtained in step C of Example 3 and 65 μl (0.91 mmol) of propionaldehyde were treated by the same procedure as described in step A of Example 3 to prepare 76 mg of the titled compound (yield=41%).

Mass spectrum (FAB-MS): m/z=614(M+H)$^+$
$^1$HNMR(CD$_3$OD, δ): 1.02(9H,m), 1.10–2.00(17H,m), 2.31(1H,m), 2.56(2H,m), 3.09(1H,m), 3.30(5H,m), 3.54 (1H,m), 4.30(1H,m), 4.94(1H,m), 5.10(1H,m), 5.31(1H,m), 5.44(1H,m), 5.97–6.03(3H,m), 6.25(2H,m), 7.07(1H,m)

Example 9

6-[3,6-Dihydroxy-10-(3-hydroxycyclohexyl)-3-(2-isopropylaminoethyl)-4-(phosphonoxy)-1,7,9-decatrienyl]-5,6-dihydro-5-ethyl-2H-pyran-2-one A portion (160 mg, 0.30 mmol) of the compound obtained in step C of Example 3 and 27 μl (0.36 mmol) of acetone were treated by the same procedure as described in step A of Example 3 to prepare 40 mg of the titled compound (yield=23%).

Mass spectrum (FAB-MS): m/z=572(M+H)$^+$
$^1$HNMR(CD$_3$OD, δ): 0.96(3H,t,J=7.4 Hz), 1.00–2.00 (20H,m), 2.22(1H,m), 2.56(2H,m), 3.07(1H,m), 3.13(1H,m), 3.55(1H,m), 4.31(1H,m), 4.94(1H,m), 5.09(1H,m), 5.31 (1H,m), 5.44(1H,m), 5.90–6.03(3H,m), 6.25(2H,m), 7.08 (1H,m)

Example 10

6-[3,6-Dihydroxy-3-(2-dipentylaminoethyl)-10-(3-hydroxycyclohexyl)-4-(phosphonoxy)-1,7,9-decatrienyl]-5,6-dihydro-5-ethyl-2H-pyran-2-one A portion (160 mg, 0.30 mmol) of the compound obtained in step C of Exmaple 3 and 96 μl (0.91 mmol) of valeryl aldehyde were treated by the same procedure as described in step A of Example 3 to prepare 53 mg of the titled compound (yield=26%).

Mass spectrum (FAB-MS): m/z=670(M+H)$^+$
$^1$HNMR(CD$_3$OD, δ): 0.95(9H,m), 1.00–2.10(25H,m), 2.25(1H,m), 2.56(1H,m), 3.09(6H,m), 3.54(1H,m), 4.30 (1H,m), 4.95(1H,m), 5.11(1H,m) 5.31(1H,m), 5.44(1H,m), 5.90–6.10(3H,m), 6.25(2H,m), 7.08(1H,m)

Example 11

6-[3,6-Dihydroxy-10-(3-hydroxycyclohexyl)-3-(2-methyloctylaminoethyl)-4-(phosphonoxy)-1,7,9-decatrienyl]-5,6-dihydro-5-ethyl-2H-pyran-2-one A portion (160 mg, 0.30 mmol) of the compound obtained in step C of Example 3 and 52 μl (0.33 mmol) of octyl aldehyde were N-octylated by the same procedure as described in step A of Example 3; without being subsequently isolated, the product was N-methylated with 35% formaldehyde solution (72 ml, 0.90 mmol) to prepare 70 mg of the titled compound (yield=35%).

Mass spectrum (FAB-MS): m/z=656(M+H)$^+$
$^1$HNMR(CD$_3$OD, δ): 0.94(3H,m), 0.99(3H,m), 1.00–2.20 (25H,m), 2.28(1H,m), 2.56(2H,m), 2.82(3H,s), 3.09(4H,m), 3.54(1H,m), 4.31(1H,m), 4.95(1H,m), 5.10(1H,m), 5.31 (1H,m), 5.44(1H,m), 6.00–6.20(3H,m), 6.25(2H,m), 7.08 (1H,m)

Example 12

6-[3,6-Dihydroxy-10-(3-hydroxycyclohexyl)-3-(2-pentylaminoethyl)-4-(phosphonoxy)-1,7,9-decatrienyl]-5,6-dihydro-5-ethyl-2H-pyran-2-one A portion (160 mg, 0.30 mmol) of the compound obtained in step C of Example 3 and 38 μl (0.36 mmol) of valeryl aldehyde were treated by the same procedure as described in step A of Exmaple 3 to prepare 84 mg of the titled compound (yield=46%).

Mass spectrum (FAB-MS): m/z=600(M+H)$^+$ $^1$HNMR(CD$_3$OD, δ): 0.95(6H,m), 1.05–2.10(19H,m), 2.22(1H,m), 2.56(2H,m), 2.97(2H,m), 3.09(1H,m), 3.15 (1H,m), 3.54(1H,m), 4.31(1H,m), 4.94(1H,m), 5.10(1H,m), 5.31(1H,m), 5.44(1H,m), 5.90–6.20(3H,m), 6.25(2H,m), 7.08(1H,m)

Example 13

6-[3-(2-Cyclopentylaminoethyl)-3,6-dihydroxy-10-(3-hydroxycyclohexyl)-4-(phosphonoxy)-1,7,9-decatrienyl]-5,6-dihydro-5-ethyl-2H-pyran-2-one A portion (160 mg, 0.30 mmol) of the compound obtained in step C of Exmaple 3 and 32 μl (0.36 mmol) of cyclopentanone were treated by the same procedure as described in step A of Example 3 to prepare 152 mg of the titled compound (yield=84%).

Mass spectrum (FAB-MS): m/z=598(M+H)$^+$ $^1$HNMR(CD$_3$OD, δ): 0.96(3H,m), 1.00–2.10(21H,m), 2.21(1H,m), 2.57(2H,m), 3.05(1H,m), 3.14(1H,m), 3.52 (2H,m), 4.30(1H,m), 4.89(1H,m), 5.11(1H,m), 5.31(1H,m), 5.44(1H,m), 5.90–6.20 (3H,m), 6.27(2H,m), 7.10(1H,m)

Example 14

6-[3-(2-Cyclohexylaminoethyl)-3,6-dihydroxy-10-(3-hydroxycyclohexyl)-4-(phosphonoxy)-1,7,9-decatrienyl]-5,6-dihydro-5-ethyl-2H-pyran-2-one A portion (160 mg, 0.30 mmol) of the compound obtained in step C of Example 3 and 38 μl (0.36 mmol) of cyclohexanone were treated by the same procedure as described in step A of Example 3 to prepare 146 mg of the titled compound (yield=79%).

Mass spectrum (FAB-MS): m/z=612(M+H)$^+$ $^1$HNMR(CD$_3$OD, δ): 0.96(3H,t,J=7.4 Hz), 1.00–2.10 (23H,m), 2.21(1H,m), 2.56(2H,m), 3.08(2H,m), 3.15(1H, m), 3.54(1H,m), 4.30(1H,m), 4.97(1H,m), 5.11(1H,m), 5.31 (1H,m), 5.43(1H,m), 5.90–6.20(3H,m), 6.27(2H,m), 7.11 (1H,m)

Example 15

6-[3,6-Dihydroxy-10-(3-hydroxycyclohexyl)-3-(2-methylpentylaminoethyl)-4-(phosphonoxy)-1,7,9-decatrienyl]-5,6-dihydro-5-ethyl-2H-pyran-2-one A portion (100 mg, 0.17 mmol) of the compound obtained in Example 12 and 20 μl (0.25 mmol) of 35% formaldehyde solution were treated by the same procedure as described in step A of Example 3 to prepare 80 mg of the titled compound (yield 78%).

Mass spectrum (FAB-MS): m/z=614(M+H)$^+$ $^1$HNMR(CD$_3$OD, δ): 0.96(6H,m), 1.00–2.10(19H,m), 2.28(1H,m), 2.57(2H,m), 2.83(3H,s), 3.09(3H,m), 3.31(1H, m), 3.55(1H,m), 4.31(1H,m), 4.95(1H,m), 5.10(1H,m), 5.32 (1H,m), 5.43(1H,m), 6.00–6.20(3H,m), 6.27(2H,m), 7.09 (1H,m)

Example 16

6-[3,6-Dihydroxy-10-(3-hydroxycyclohexyl)-3-( 2-pentan-3-yl-aminoethyl)-4-(phosphonoxy)-1,7,9-decatrienyl]-5,6-dihydro-5-ethyl-2H-pyran-2-one A portion (160 mg, 0.30 mmol) of the compound obtained in Example 12 and 37 μl (0.36 mmol) of 3-pentanone were treated by the same procedure as described in step A of Example 3 to prepare 141 mg of the titled compound (yield=78%).

Mass spectrum (FAB-MS): m/z=600(M+H)$^+$ $^1$HNMR(CD$_3$OD, δ): 0.98(9H,m), 1.00–2.10(17H,m), 2.25(1H,m), 2.56(2H,m), 3.02(1H,m), 3.12(2H,m), 3.54 (1H,m), 4.29(1H,m), 4.96(1H,m), 5.11(1H,m), 5.31(1H,m), 5.43(1H,m), 5.90–6.20(3H,m), 6.27(2H,m), 7.08(1H,m)

Example 17

6-[3,6-Dihydroxy-10-(3-hydroxycyclohexyl)-3-(2-methylisopropylaminoethyl)-4-(phosphonoxy)-1,7,9-decatrienyl]-5,6-dihydro-5-ethyl-2H-pyran-2-one A portion (114 mg, 0.20 mmol) of the compound obtained in Example 9 and 50 μl (0.60 mmol) of 35% formaldehyde solution were treated by the same procedure as described in step A of Example 3 to prepare 95 mg of the titled compound (yield =80%).

Mass spectrum (FAB-MS): m/z=586(M+H)$^+$ $^1$HNMR(CD$_3$OD, δ): 0.95(3H,t,J=7.4 Hz), 1.00–1.81 (17H,m), 1.24(3H,d,J=6.6 Hz), 1.26(3H,d,J=6.6 Hz), 2.41 (2H,m), 2.54(2H,m), 2.67(3H,s), 3.02(1H,m), 3.16(1H,m), 3.51(2H,m), 4.27(1H,m), 5.02(1H,m), 5.08(1H,m), 5.27 (1H,m), 5.44(1H,m), 5.94–6.13(3H,m), 6.25(2H,m), 7.06 (1H,m)

Example 18

6-[3-(2-Dibutylaminoethyl)-3,6-dihydroxy-10-(3-hydroxycyclohexyl)-4-(phosphonoxy)-1,7,9-decatrienyl]- 5,6-dihydro-5-ethyl-2H-pyran-2-one A portion (130 mg, 0.25 mmol) of the compound obtained in step C of Example 3 and 72 mg (1.0 mmol) of butyl aldehyde were treated by the same procedure as described in step A of Example 3 to prepare 80 mg of the titled compound (yield 50%).

Mass spectrum (FAB-MS): m/z=642(M+H)$^+$ $^1$HNMR(CD$_3$OD, δ): 0.95–1.02(9H,m), 1.12–2.00(28H, m), 2.29(1H,m), 2.56(2H,m), 3.11(4H,m), 3.54(1H,m), 4.30 (1H,m), 4.96(1H,m), 5.11(1H,m), 5.31(1H,m), 5.44(1H,m), 5.97–6.10(3H,m), 6.25(2H,m), 7.08(1H,m)

Example 19

6-[3-[2-(1,3-Dihydroxyisopropylaminoethyl)]-3,6-dihydroxy-10-(3-hydroxycyclohexyl)-4-(phosphonoxy)-1,7,9-decatrienyl]-5,6-dihydro-5-ethyl-2H-pyran-2-one A portion (53 mg, 0.10 mmol) of the compound obtained in step C of Example 3 and 22 mg (0.12 mmol) of dihydroxyacetone (dimer) were treated by the same procedure as described in step A of Example 3 to prepare 50 mg of the titled compound (yield=80%).

Mass spectrum (FAB-MS): m/z=604(M+H)$^+$ $^1$HNMR(CD$_3$OD, δ): 0.97(3H,t,J=7.4 Hz), 1.00–2.00 (13H,m), 2.34(1H,m), 2.56(2H,m), 3.25(2H,m), 3.37(1H, m), 3.55(1H,m), 3.72(2H,m), 3.82(2H,m), 4.31(1H,m), 4.97 (1H,m), 5.11(1H,m), 5.31(1H,m), 5.45(1H,m), 5.94–6.14 (3H,m), 6.27(2H,m), 7.09(1H,m)

Example 20

6-[3-(2-Diethanolaminoethyl)-3,6-dihydroxy-10-(3-hydroxycyclohexyl)-4-(phosphonoxy)-1,7,9-decatrienyl]-5,6-dihydro-5-ethyl-2H-pyran-2-one A portion (160 mg, 0.30 mmol) of the compound obtained in step C of Example 3 and 87 mg (0.73 mmol) of hydroxyacetaldehyde were treated by the same procedure as described in step A of Example 3 to prepare 182 mg of the titled compound (yield=98%).

Mass spectrum (FAB-MS): m/z=618(M+H)$^+$ $^1$HNMR(CD$_3$OD, δ): 1.96(3H,t,J=7.4 Hz), 1.10–1.94 (14H,m), 2.35(1H,m), 2.55(2H,m), 2.96(2H,m), 3.09(2H, m), 3.19(1H,m), 3.54(1H,m), 3.79(4H,m), 4.30(1H,m), 5.01 (1H,m), 5.09(1H,m), 5.29(1H,m), 5.44(1H,m), 5.94–6.13 (3H,m), 6.25(2H,m), 7.07(1H,m)

Example 21

6-[3,6-Dihydroxy-10-(3-hydroxycyclohexyl)-4-(phosphonoxy)-3-[2-(1-pyridiniumisopropylaminoethyl)]-1,7,9-decatrienyl]-5,6-dihydro-5-ethyl-2H-pyran-2-one A portion (62 mg, 0.12 mmol) of the compound obtained in step C of Example 3 and 87 mg (0.51 mmol) of 1-acetonylpyridinium chloride were treated by the same procedure as described in step A of Example 3 to prepare 30 mg of the titled compound (yield=39%).

Mass spectrum (FAB-MS): m/z=650(M+H)$^+$
$^1$HNMR(CD$_3$OD, δ): 0.93(3H,m), 1.16(3H,m), 1.00–1.91 (14H,m), 2.53(2H,m), 2.60–2.91(3H,m), 3.47(1H,m), 4.16 (1H,m), 4.41(1H,m), 4.64(1H,m), 4.92(1H,m), 5.04(1H,m), 5.29(1H,m), 5.41(1H,m), 5.91(2H,m), 6.00(1H,m), 6.24 (2H,m) 7.07(1H,m), 8.12(2H,m), 8.59(1H,m), 8.93(2H,m)

Example 22

6-[3,6-Dihydroxy-10-(3-hydroxycyclohexyl)-4-(phosphonoxy)-3-(2-trimethylammoniumethyl)-1,7,9-decatrienyl]-5,6-dihydro-5-ethyl-2H-pyran-2-one A portion (190 mg, 0.34 mmol) of the compound obtained in Exmaple 3 and 43 μl (0.68 mmol) of methyl iodide were dissolved in 2 ml of dimethylformamide and stirred at room temperature for 1.5 hr. The solvent was removed under vacuum to give a crude product, which was separated by high-performance liquid chromatography. The peaks of interest were combined, deacidified on SepPack C18 and freeze-dried to prepare 80 mg of the titled compound (yield=41%).

Mass spectrum (FAB-MS): m/z=572(M+H)$^+$
$^1$HNMR(CD$_3$OD, δ): 0.95(3H,m), 1.00–1.98(14H,m), 2.25(1H,m), 2.56(2H,m), 3.10(9H,s), 3.54(2H,m), 4.25(1H, m), 5.08(2H,m), 5.26(1H,m), 5.42(1H,m), 5.90–6.10(3H, m), 6.25(2H,m) 7.08(1H,m),

Example 23

6-[3,6-Dihydroxy-10-(3-hydroxycyclohexyl)-4-(phosphonoxy)-3-(2-trimethylammoniumethyl)-1,7,9-decatrienyl]-5,6-dihydro-5-ethyl-2H-pyran-2-one A portion (62 mg, 0.12 mmol) of the compound obtained in step C of Example 3 and 46 μl (0.84 mmol) of methyl iodide were treated by the same procedure as described in Example 22 to prepare 40 mg of the titled compound (yield=58%).

Example 24

6-[3-(2-Allylaminoethyl)-3,6-dihydroxy-10-(3-hydroxycyclohexyl)-4-(phosphonoxy)-1,7,9-decatrienyl]-5,6-dihydro-5-ethyl-2H-pyran-2-one A portion (87 mg, 0.16 mmol) of the compound obtained in step C of Example 3, 111 μl (1.28 mmol) of allyl bromide and 280 μl (1.60 mmol) of diisopropylethylamine were dissolved in 8 ml of methanol and stirred at 50° C. for 4 hr. The solvent was removed under vacuum to give a crude product, which was separated by high-performance liquid chromatography. The peaks of interest were combined, deacidified on SepPack C18 and freeze-dried to prepare 6 mg of the titled compound (yield=7%).

Mass spectrum (FAB-MS): m/z=570(M+H)$^+$
$^1$HNMR(CD$_3$OD, δ): 0.95(3H,m), 1.05–1.95(13H,m), 2.26(1H,m), 2.56(2H,m), 3.06(1H,m), 3.16(1H,m), 3.15 (1H,m), 3.55(1H,m), 3.63(2H,m), 4.31(1H,m), 4.94(1H,m), 5.10(1H,m), 5.31(1H,m), 5.42–5.54(3H,m), 5.87–6.09(4H, m) 6.27(2H,m), 7.08(1H,m),

Example 25

6-[3-(2-Diallylaminoethyl)-3,6-dihydroxy-10-(3-hydroxycyclohexyl)-4-(phosphonoxy)-1,7,9-decatrienyl]-5,6-dihydro-5-ethyl-2H-pyran-2-one The same procedure as described in Example 24 was followed to prepare 22 mg of the titled compound (yield= 23%).

Mass spectrum (FAB-MS): m/z=610(M+H)$^+$
$^1$HNMR(CD$_3$OD, δ): 0.95(3H,m), 1.05–1.95(14H,m), 2.06(1H,m), 2.30(1H,m), 2.56(2H,m), 3.06(1H,m), 3.55 (1H,m), 3.63–3.81(4H,m), 4.31(1H,m), 4.94(1H,m), 5.10 (1H,m), 5.31(1H,m), 5.44(1H,m), 5.57–5.61(4H,m) 5.91–6.06(4H,m), 6.27(2H,m) 7.08(1H,m)

Example 26

6-[3,6-Dihydroxy-10-(3-hydroxycyclohexyl)-4-(phosphonoxy)-3-(2-triallylammoniumethyl)-1,7,9-decatrienyl]-5,6-dihydro-5-ethyl-2H-pyran-2-one The same procedure as described in Example 24 was followed to prepare 20 mg of the titled compound (yield= 19%).

Mass spectrum (FAB-MS): m/z=651(M+H)$^+$
$^1$HNMR(CD$_3$OD, δ): 0.96(3H,m), 1.05–1.95(12H,m), 2.18–2.35(2H,m), 2.57(2H,m), 3.13(1H,m), 3.41(1H,m), 3.56(1H,m), 3.93(6H,m), 4.28(1H,m), 4.95(1H,m), 5.09 (1H,m), 5.31(1H,m), 5.44(1H,m), 5.71–5.77(6H,m), 5.99–6.08(6H,m), 6.25(2H,m) 7.08(1H,m)

We claim:

1. A compound represented by the general formula (I):

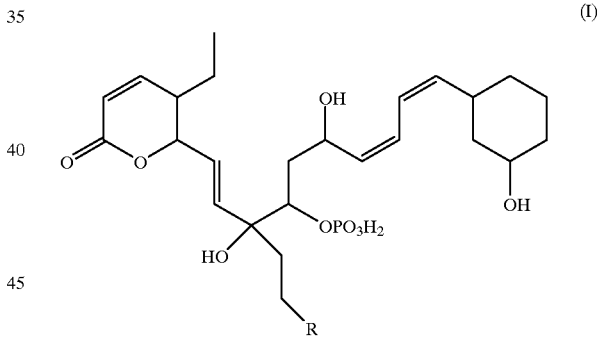

(where R is a group —NHCHR$_1$R$_2$, —N(CHR$_1$R$_2$)$_2$, —N(CHR$_1$R$_2$)CHR$_3$R$_4$, —N$^+$(CHR$_1$R$_2$)$_3$, —N$^+$(CHR$_1$R$_2$)$_2$CHR$_3$R$_4$ or —N$^+$(CHR$_1$R$_2$)(CHR$_3$R$_4$)CHR$_5$R$_6$ (where R$_1$, R$_2$, R$_3$, R$_4$, R$_5$ and R$_6$, which may be the same or different, are each a hydrogen atom, an alkyl group, an alkenyl group, an aryl group or an aralkyl group, or an alkyl, alkenyl, aryl or aralkyl group which is substituted by at least one substituent selected from the group consisting of a halogen atom, a hydroxyl group, a lower alkoxy group, a lower alkylacyloxy group, a lower alkylacyl group, a lower alkoxycarbonyl group, a nitro group, and a cyano group, with CHR$_1$R$_2$, CHR$_3$R$_4$ or CHR$_5$R$_6$ optionally forming a cyclic alkyl group, provided that R is not —NHCH$_3$, and that when R is —N(CHR$_1$R$_2$)CHR$_3$R$_4$, —N$^+$(CHR$_1$R$_2$)$_2$CHR$_3$R$_4$ or —N$^+$(CHR$_1$R$_2$)(CHR$_3$R$_4$)CHR$_5$R$_6$, CHR$_1$R$_2$, CHR$_3$R$_4$ and CHR$_5$R$_6$ are different groups)) or a pharmacologically acceptable salt thereof.

2. A compound represented by the general formula (II):

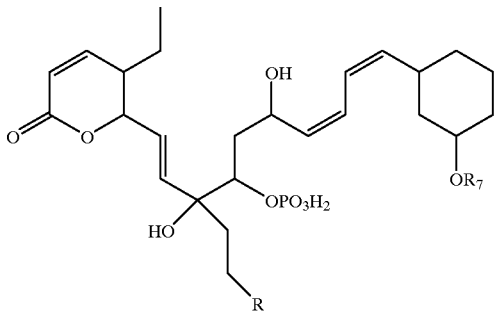

(II)

(where R is a group —NHCHR$_1$R$_2$, —N(CHR$_1$R$_2$)$_2$, —N(CHR$_1$R$_2$)CHR$_3$R$_4$, —N$^+$(CHR$_1$R$_2$)$_3$, —N$^+$(CHR$_1$R$_2$)$_2$CHR$_3$R$_4$ or —N$^+$(CHR$_1$R$_2$)(CHR$_3$R$_4$)CHR$_5$R$_6$ (where R$_1$, R$_2$, R$_3$, R$_4$, R$_5$ and R$_6$, which may be the same or different, are each a hydrogen atom, an alkyl group, an alkenyl group, an aryl group or an aralkyl group, or an alkyl, alkenyl, aryl or aralkyl group which is substituted by at least one substituent selected from the group consisting of a halogen atom, a hydroxyl group, a lower alkoxy group, a lower alkylacyloxy group, a lower alkylacyl group, a lower alkoxycarbonyl group, a nitro group, and a cyano group, with CHR$_1$R$_2$, CHR$_3$R$_4$ or CHR$_5$R$_6$ optionally forming a cyclic alkyl group, provided that R is not —NHCH$_3$, and that when R is —N(CHR$_1$R$_2$)CHR$_3$R$_4$, —N$^+$(CHR$_1$R$_2$)$_2$CHR$_3$R$_4$ or —N$^+$(CHR$_1$R$_2$)(CHR$_3$R$_4$)CHR$_5$R$_6$, CHR$_1$R$_2$, CHR$_3$R$_4$ and CHR$_5$R$_6$ are different groups); and R$_7$ is an acyl group, or a salt thereof.

3. A compound represented by the general formula (II):

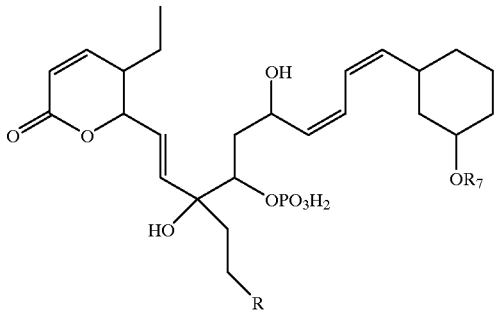

(II)

(where R is a group —NHCHR$_1$R$_2$, —N(CHR$_1$R$_2$)$_2$, —N(CHR$_1$R$_2$)CHR$_3$R$_4$, —N$^+$(CHR$_1$R$_2$)$_3$, —N$^+$(CHR$_1$R$_2$)$_2$CHR$_3$R$_4$ or —N$^+$(CHR$_1$R$_2$)(CHR$_3$R$_4$)CHR$_5$R$_6$ (where R$_1$, R$_2$, R$_3$, R$_4$, R$_5$ and R$_6$, which may be the same or different, are each a hydrogen atom, an alkyl group, an alkenyl group, an aryl group or an aralkyl group, or an alkyl, alkenyl, aryl or aralkyl group which is substituted by at least one substituent selected from the group consisting of a halogen atom, a hydroxyl group, a lower alkoxy group, a lower alkylacyloxy group, a lower alkylacyl group, a lower alkoxycarbonyl group, a nitro group, a cyano group and a heterocyclic group, with CHR$_1$R$_2$, CHR$_3$R$_4$ or CHR$_5$R$_6$ optionally forming a cyclic alkyl group, provided that R is not —NHCH$_3$, and that when R is —N(CHR$_1$R$_2$)CHR$_3$R$_4$, —N$^+$(CHR$_1$R$_2$)$_2$CHR$_3$R$_4$ or —N$^+$(CHR$_1$R$_2$)(CHR$_3$R$_4$)CHR$_5$R$_6$, CHR$_1$R$_2$, CHR$_3$R$_4$ and CHR$_5$R$_6$ are different groups); and R$_7$ is a butyryl group, an isobutyryl group, an isovaleryl group, a 2-methylbutyryl group, a 4-methylvaleryl group, a cyclohexanecarbonyl group, a 4-methylhexanoyl group, a 5-methylhexanoyl group, a 6-methylheptanoyl group, a cyclohexylethylcarbonyl group, an octanoyl group, a 6-methyloctanoyl group or a 7-methyloctanoyl group) or a salt thereof.

4. A compound according to claim 1, wherein R in the general formula (I) is —NHCHR$_1$R$_2$, provided that R$_1$ is not a hydrogen atom when R$_2$ is a hydrogen atom, or a pharmacologically acceptable salt thereof.

5. A compound according to claim 1, wherein R in the general formula (I) is —N(CHR$_1$R$_2$)CHR$_3$R$_4$, or a pharmacologically acceptable salt thereof.

6. A compound according to claim 1, wherein R in the general formula (I) is —N(CHR$_1$R$_2$)$_2$ or a pharmacologically acceptable salt thereof.

7. A compound according to claim 1, wherein R in the general formula (I) is —N$^+$(CHR$_1$R$_2$)$_3$ or a pharmacologically acceptable salt thereof.

8. A compound according to claim 1, wherein R in the general formula (I) is —N$^+$(CHR$_1$R$_2$)$_2$CHR$_3$R$_4$, or a pharmacologically acceptable salt thereof.

9. A compound according to claim 1, wherein R in the general formula (I) is —N$^+$(CHR$_1$R$_2$)(CHR$_3$R$_4$)CHR$_5$R$_6$, or a pharmacologically acceptable salt thereof.

10. A compound according to claim 1, which is selected from the following compounds:
6-[3,6-Dihydroxy-3-(2-dimethylaminoethyl)-10-(3-hydroxycyclohexyl)-4-(phosphonoxy)-1,7,9-decatrienyl]-5,6-dihydro-5-ethyl-2H-pyran-2-one;
6-[3-(2-Diethylaminoethyl)-3,6-dihydroxy-10-(3-hydroxycyclohexyl)-4-(phosphonoxy)-1,7,9-decatrienyl]-5,6-dihydro-5-ethyl-2H-pyran-2-one;
6-[3,6-Dihydroxy-3-(2-dipropylaminoethyl)-10-(3-hydroxycyclohexyl)-4-(phosphonoxy)-1,7,9-decatrienyl]-5,6-dihydro-5-ethyl-2H-pyran-2-one;
6-[3,6-Dihydroxy-10-(3-hydroxycyclohexyl)-3-(2-isopropylaminoethyl)-4-(phosphonoxy)-1,7,9-decatrienyl]-5,6-dihydro-5-ethyl-2H-pyran-2-one;
6-[3,6-Dihydroxy-10-(3-hydroxycyclohexyl)-3-(2-pentylaminoethyl)-4-(phosphonoxy)-1,7,9-decatrienyl]-5,6-dihydro-5-ethyl-2H-pyran-2-one;
6-[3-(2-Cyclopentylaminoethyl)-3,6-dihydroxy-10-(3-(hydroxycyclohexyl)-4-(phosphonoxy)-1,7,9-decatrienyl]-5,6-dihydro-5-ethyl-2H-pyran-2-one;
6-[3-(2-Cyclohexylaminoethyl)-3,6-dihydroxy-10-(3-hydroxycyclohexyl)-4-(phosphonoxy)-1,7,9-decatrienyl]-5,6-dihydro-5-ethyl-2H-pyran-2-one;
6-[3,6-Dihydroxy-10-(3-hydroxycyclohexyl)-3-(2-pentan-3-yl-aminoethyl)-4-(phosphonoxy)-1,7,9-decatrienyl]-5,6-dihydro-5-ethyl-2H-pyran-2-one;
6-[3,6-Dihydroxy-10-(3-hydroxycyclohexyl)-3-(2-methyl-isopropylaminoethyl)-4-(phosphonoxy)-1,7,9-decatrienyl]-5,6-dihydro-5-ethyl-2H-pyran-2-one;
6-[3-[2-(1,3-Dihydroxyisopropylaminoethyl)]-3,6-dihydroxy-10-(3-hydroxycyclohexyl)-4-(phosphonoxy)-1,7,9-decatrienyl]-5,6-dihydro-5-ethyl-2H-pyran-2-one;
6-[3-(2-Diethanolaminoethyl)-3,6-dihydroxy-10-(3-hydroxycyclohexyl)-4-(phosphonoxy)-1,7,9-decatrienyl]-5,6-dihydro-5-ethyl-2H-pyran-2-one;
6-[3,6-Dihydroxy-10-(3-hydroxycyclohexyl)-4-(phosphonoxy)-3-(2-trimethylammoniumethyl)-1,7,9-decatrienyl]-5,6-dihydro-5-ethyl-2H-pyran-2-one;
6-[3,6-Dihydroxy-10-(3-hydroxycyclohexyl)-4-(phosphonoxy)- 3-(2-triallylammoniumethyl)-1,7,9-decatrienyl]-5,6-dihydro-5-ethyl-2H-pyran-2-one, or a pharmacologically acceptable salt thereof.

11. A Process which comprises subjecting compounds, either singly or in admixture, that are represented by the general formula (III):

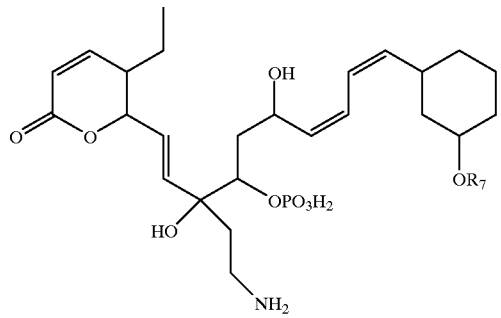

(where $R_7$ is an acyl group) to reductive alkylation reaction with a ketone or aldehyde of the general formula $R_1COR_2$ and/or $R_3COR_4$ (where $R_1$, $R_2$, $R_3$ and $R_4$, which may be the same or different, are each a hydrogen atom, an alkyl group, an alkenyl group, an aryl group or an aralkyl group, or an alkyl, alkenyl, aryl or aralkyl group which is substituted by at least one substituent selected from the group consisting of a halogen atom, a hydroxyl group, a lower alkoxy group, a lower alkylacyloxy group, a lower alkylacyl group, a lower alkoxycarbonyl group, a nitro group, and a cyano group, with $R_1$ and $R_2$ or $R_3$ and $R_4$ being optionally taken together to form an alkylene group, provided that $R_1COR_2$ is different from $R_3COR_4$, and that $R_1$ is not a hydrogen atom when $R_2$ is a hydrogen atom) in the presence of a reducing agent, to thereby produce a compound represented by the general formula (IIa) or a salt thereof:

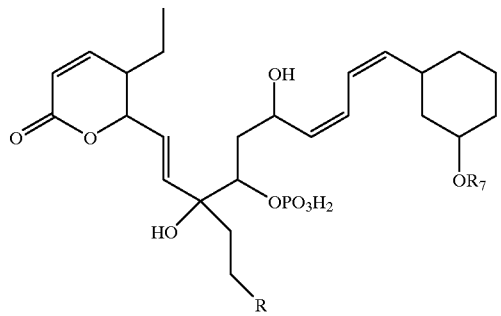

(where R is a group —$NHCHR_1R_2$, —$N(CHR_1R_2)_2$ or —$N(CHR_1R_2)CHR_3R_4$ (where $R_1$, $R_2$, $R_3$ and $R_4$ are the same as defined above)).

12. A process which comprises subjecting a compound represented by the general formula (IV):

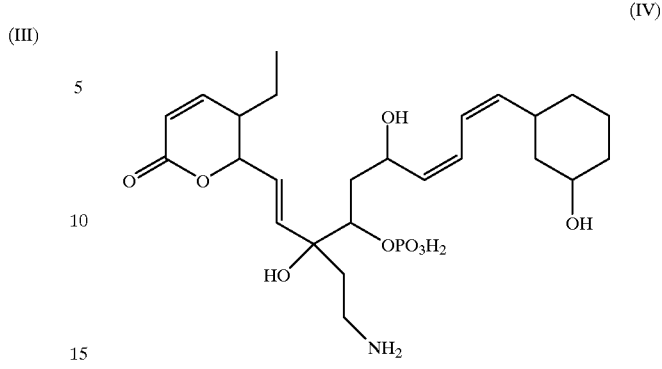

to reductive alkylation reaction with a ketone or aldehyde of the general formula $R_1COR_2$ and/or $R_3COR_4$ (where $R_1$, $R_2$, $R_3$, and $R_4$, which may be the same or different, are each a hydrogen atom, an alkyl group, an alkenyl group, an aryl group or an aralkyl group, or an alkyl, alkenyl, aryl or aralkyl group which is substituted by at least one substituent selected from the group consisting of a halogen atom, a hydroxyl group, a lower alkoxy group, a lower alkylacyloxy group, a lower alkylacyl group, a lower alkoxycarbonyl group, a nitro group, and a cyano group, with $R_1$ and $R_2$ or $R_3$ and $R_4$ being optionally taken together to form an alkylene group, provided that $R_1COR_2$ is different from $R_3COR_4$, and that $R_1$ is not a hydrogen atom when $R_2$ is a hydrogen atom) in the presence of a reducing agent, to thereby prepare a compound represented by the general formula (Ia) or a pharmacologically acceptable salt thereof:

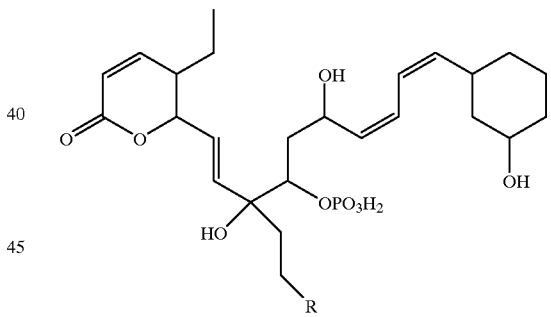

(where R is a group —$NHCHR_1R_2$, —$N(CHR_1R_2)_2$ or —$N(CHR_1R_2)CHR_3R_4$ (where $R_1$, $R_2$, $R_3$ and $R_4$ are the same as defined above)).

13. A therapeutic agent for thrombocytopenia containing as an effective ingredient the compound of claim 1 or a pharmacologically acceptable salt thereof.

* * * * *